(12) United States Patent
Wang et al.

(10) Patent No.: US 7,453,565 B2
(45) Date of Patent: Nov. 18, 2008

(54) SUBSTRATE FOR SURFACE-ENHANCED RAMAN SPECTROSCOPY, SERS SENSORS, AND METHOD FOR PREPARING SAME

(75) Inventors: Yuh-Lin Wang, Taipei (TW); Huai-Hsien Wang, Tainan County (TW); Chih-Yi Liu, Taipei County (TW); Juen-Kai Wang, Taipei (TW)

(73) Assignee: Academia Sinica, Taipei (TW)

( * ) Notice: Subject to any disclaimer, the term of this patent is extended or adjusted under 35 U.S.C. 154(b) by 156 days.

(21) Appl. No.: 11/423,818

(22) Filed: Jun. 13, 2006

(65) Prior Publication Data
US 2007/0285657 A1 Dec. 13, 2007

(51) Int. Cl.
G01J 3/44 (2006.01)
G01N 21/65 (2006.01)

(52) U.S. Cl. .................................... 356/301
(58) Field of Classification Search .................. 356/301
See application file for complete search history.

(56) References Cited
U.S. PATENT DOCUMENTS
2005/0105085 A1* 5/2005 Naya .......................... 356/301

OTHER PUBLICATIONS
Yao et al., Pure Appl. Chem., vol. 72, No. 1, pp. 221-228, 2000.*

* cited by examiner

*Primary Examiner*—F. L Evans
(74) *Attorney, Agent, or Firm*—Pantich Schwarze Belisario & Nadel LLP

(57) ABSTRACT

This invention relates to methods of preparing substrates that enhance the Raman signal of analytes in surface-enhanced Raman spectroscopy (SERS). The SERS-active substrate comprises an array of metal nanoparticles at least partially embedded in a template. The substrate's uniform and readily reproducible SERS-active properties with a wide range of analyte concentrations substantially enhance the power and utility of SERS. This invention also provides sensors, as well as Raman instruments, comprising the SERS-active substrates.

12 Claims, 6 Drawing Sheets

SUBSTRATE FOR SURFACE-ENHANCED RAMAN SPECTROSCOPY, SERS SENSORS, AND METHOD FOR PREPARING SAME

BACKGROUND OF THE INVENTION

Raman spectroscopy, which involves an inelastic scattering of photons by chemical entities, has been widely used as a tool for the identification of various chemical substances such as diamond, drugs, and biomolecules, as well as for investigation into adsorbed molecules on surfaces. However, the detection sensitivity of Raman spectroscopy and therefore its applications are often limited by the weak signal(s) associated with the intrinsically small Raman scattering cross-sections.

Since 1974, the discovery of surface-enhanced Raman spectroscopy, capable of strengthening the Raman signal and facilitating the identification of vibrational signatures of molecules in chemical and biological systems, has drawn substantial attention in the relevant field. Recently, the introduction of single-molecule Raman scattering further enhanced the Raman detection sensitivity, thereby broadening the scope of sensor applications involving SERS.

A SERS-active substrate based on nanosphere lithography-derived Ag particles, which has adjustable surface plasmon resonance properties, has been demonstrated (Hynes, C. L.; Van Duyne, R. P. *J. Phys. Chem.* B 2003, 107, 7426; Jensen, T. R.; Schatz, G. C.; Van Duyne, R. P. *J. Phys. Chem. B* 1999, 103, 2394). Xu et al. provided a theoretical study in 2000 that the effective Raman cross section of a molecule placed between two metal nanoparticles could be enhanced by more than 12 orders of magnitude (Xu, H.; Aizpurua, J.; Käll, M.; Apell, P. *Phys. Rev. E* 2000, 62, 4318). The field enhancement for SERS from metal nanoparticle arrays has also been theoretically investigated. Specifically, it was proposed that very localized plasmon modes, created by strong electromagnetic coupling between two adjacent metallic objects, dominate the surface enhanced Raman scattering response in an array of nanostructures (García-Vidal, F. J.; Pendry, J. B. *Phys. Rev. Lett.* 1996, 77, 1163). The interparticle coupling-induced enhancement contributes to the broadening in the width of the plasmon resonance peak, which better encompasses both the excitation wavelength and Raman peak. From the calculations of the average enhancement factor over the surfaces of an array of infinite-long Ag nanorods with semicircular cross-section, it has been shown that significant near-field interaction between adjacent nanorods takes place when the gap between the nanorods reached half (½) of their diameters.

The dependence of the enhancement factor on the gap between the adjacent nanoparticles on a SERS-active substrate has also been studied. For example, Gunnarsson et al. reported SER scattering on ordered Ag-nanoparticle arrays with interparticle gap above 75 nm (Gunnarsson, L; Bjerneld, E. J.; Xu, H.; Petronis, S. Kasemo, B.; Käll, M. *Appl. Phys. Lett.* 2001, 78, 802). Lu et al. provided the study on the temperature-controlled variation of interparticle gaps among Ag-nanoparticles embedded in a polymer membrane (Lu, Y.; Liu, G. L.; Lee, L. P. *Nano Lett.* 2005, 5, 5). Performance of SERS on self-organized Au-nanoparticle arrays with narrow interpaticle gap was investigated, and so was SERS from nanowire arrays in aluminum matrix with interparticle gaps of ~110 nm. (Wei, A.; Kim, B.; Sadtler, B.; Tripp, S. L. *Chem. Phys. Chem.* 2001, 2, 743; Sauer, G.; Brehm, G.; Schneider, S.; Graener, H.; Seifert, G.; Nielsch, K.; Choi, J.; Göring, P.; Gösele, U.; Miclea, P.; Wehrspohn, R. B. *J. Appl. Phys.* 2005, 97, 024308).

As shown by the theoretical and experimental studies above, the precise control of the gaps between the nanostructures on a SERS-active substrate to be in the sub-50 nm range is difficult with the pre-existing nanofabrication methods. It is thus the intent of this invention to control the inter-nanopit gaps to be around or below 50 nm, as that is the key to the fabrication of SERS substrates with uniformly high enhancement factor.

BRIEF SUMMARY OF THE INVENTION

It is therefore the broad objective of the present invention to provide SERS-active substrates, with uniform and controlled separation distance between adjacent particles, that enhance the power of the SERS.

One aspect of this invention provides methods of preparing a substrate with metal particles, that may be used with SERS that comprise the steps of: (a) preparing a template with an array of pits; (b) etching the template to enlarge said pits in the template, such that the adjacent, enlarged pits are separated by an inter-pit gap of 3-50 nanometers; (c) depositing particles of metals into the pits in the template; and (d) further etching the template for manifesting the particles.

In a second aspect, this invention provides a Raman sensor substrate that comprises the SERS-active substrate produced by the methods according to the above paragraph, paragraph 7.

Finally, this invention provides a Raman instrument that comprises: (a) a radiation source, (b) a detector that may be used for detecting scattered radiation, and (c) a Raman sensor comprising the SERS-active substrate produced by the methods according to paragraph 7.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 2(*b*) is a top-view scanning electron microscopy (SEM) image of an AAO substrate after deposition or adsorption of Ag-nanoparticles FIG. 2(*c*) is a histogram of D.

FIG. 2(*d*) is a histogram of W.

FIG. 2(*e*) is a TEM image of the Ag-nanoparticles.

FIG. 2(*f*) are SEM images of substrates.

DETAILED DESCRIPTION OF THE INVENTION

The present invention provides methods of preparing SERS-active substrates that enable reproducible and quantitative SERS measurements to be made in a highly efficient manner. Some of the key components of the invention include the ability to control the number and size of the pores of the substrate, as well as the size of the incorporated metal, so that the efficiencies of plasmon field generation and Raman scattering are increased substantially. This invention further provides Raman sensors as well as Raman instruments comprising SERS-active substrates produced from the disclosed methods.

The methods of preparing SERS-active substrates with metal particles, according to this invention, involve (a) preparing a template comprising an array of pits; (b) etching the template to broaden, widen, or otherwise enlarge said pits in the template, such that the resultant, adjacent pits, wells, or repository spaces are 3-50 nanometers apart; (c) depositing particles of metals into the repository spaces in the template; and (d) further etching the template for manifesting the particles.

In a preferred embodiment, the present invention provides methods of preparing SERS-active substrates with enlarged pits being no more than about 100 nanometers in diameter.

The metals for this invention are preferably silver. While silver is preferably used, other metals known to be SERS-active by one of ordinary skill in the art, such as metals belonging to Group IB of the periodic table, can also be incorporated into the template.

In yet another embodiment, this invention provides methods of preparing SERS-active substrates according to paragraphs 24-26, wherein said step (c) comprises electrochemically plating the metal particles onto the template.

Also in accordance with the present invention is a preferred embodiment which provides methods of preparing SERS-active substrates according to paragraphs 24-26, wherein the preparation of said template with an array of pits comprises anodizing the template.

In another embodiment, the template for this invention is an anodic aluminum oxide (AAO) template.

Figure 1:
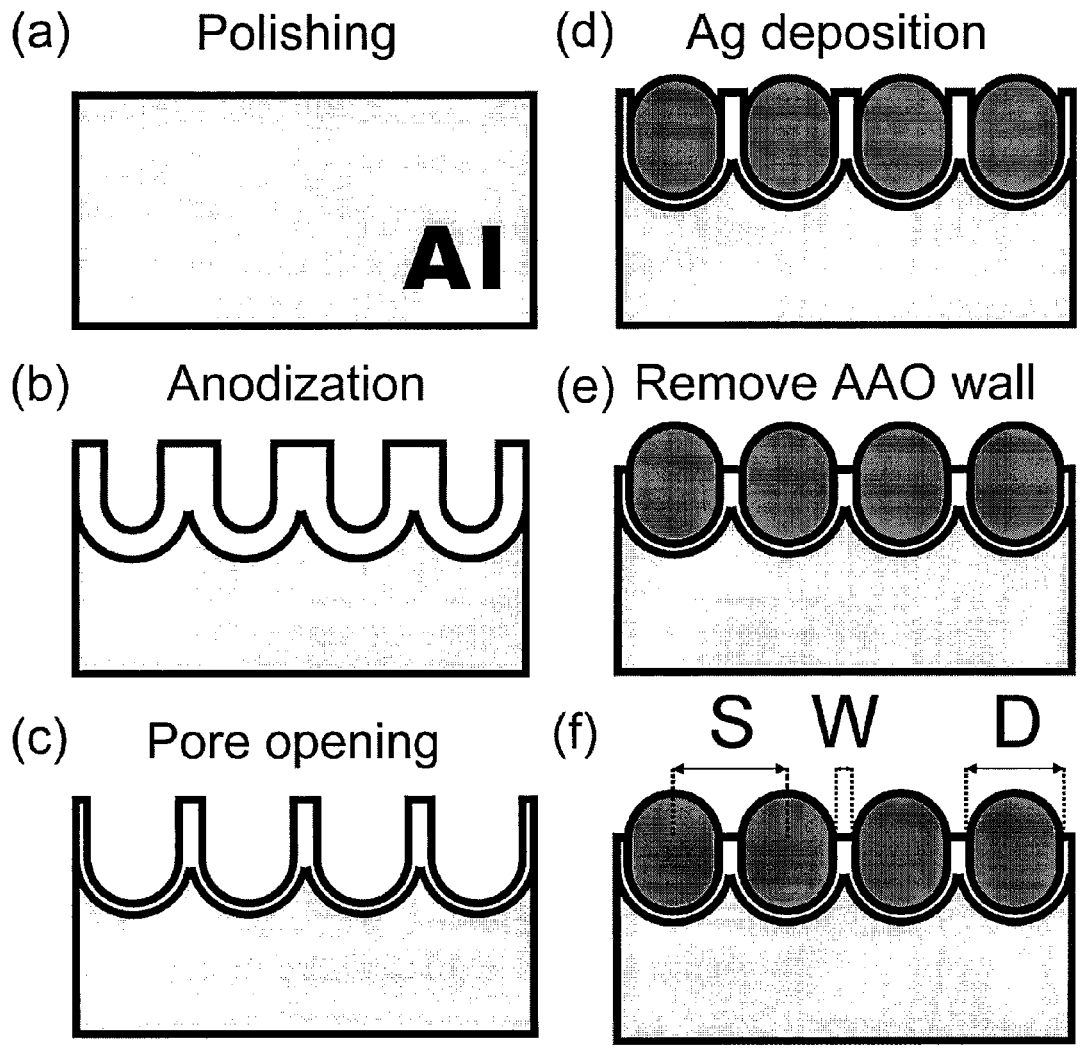
FIG. 1 is a schematic diagram showing the process for fabricating metal-filled porous anodic alumina substrates.

For example, FIG. 1 is a schematic diagram showing the process for fabricating silver-filled porous anodic alumina substrates. Preferably, an aluminum foil are polished and anodized first. The aluminum foil can then be etched, causing the pores to "open," or enlarge. Following the "pore opening" is the deposition of Ag particles onto the anodic aluminum oxide (AAO) template.

Figure 2:
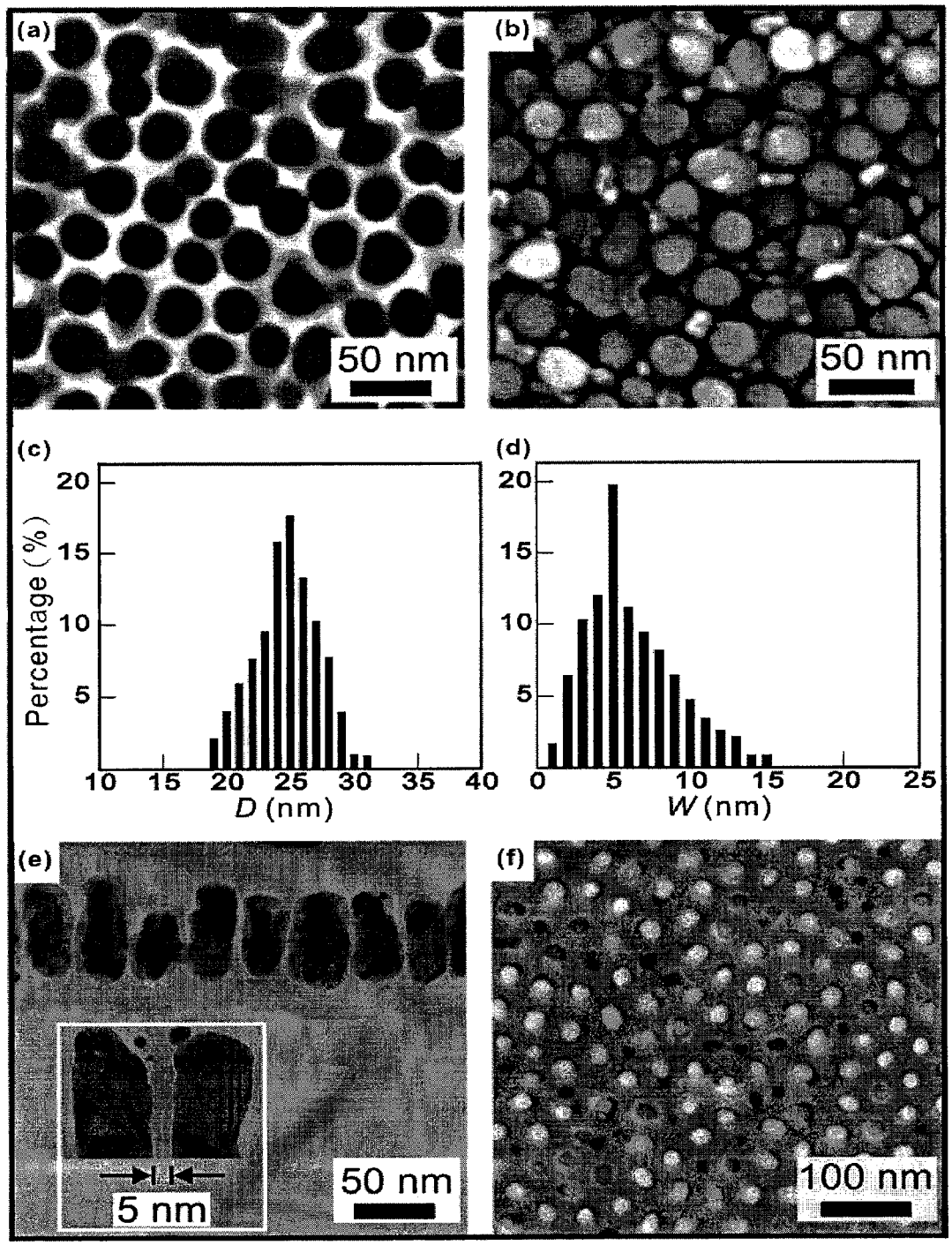
FIG. 2(*a*) is a top-view scanning electron microscopy (SEM) image of an anodic aluminum oxide (AAO) substrate before deposition or adsorption of Ag-nanoparticles.

As illustrated by FIGS. 2(a) to 2(f), the size and concentration of the pits not only may be optimally configured for highly effective SERS, their parameters can also be controlled by the present invention. FIGS. 2(a) and 2(b) show top-view images of a typical Ag/AAO substrate before and after the growth of Ag-nanoparticles, respectively, whose pits have been widened to 25 nm in diameter by etching. Such images taken by a field emission scanning electron microscope (SEM) with a beam diameter of 1 nm (JEOL 6700) are analyzed by a commercial software (Scanning Probe Image Processor, Image Metrology) to determine the distribution and spread of an array's metal particle diameter (D) and interparticle gap (W) as shown by FIGS. 2(c) and 2(d), respectively. The size measurements are further confirmed by cross-sectional transmission electron microscopy images, as exemplified by FIG. 2(e). The results showed a fabrication of Ag-nanoparticle arrays with a mean W as small as 5±2 nm. To further demonstrate the flexibility and precision of the fabrication process, FIG. 2(f) shows the SEM image of a substrate with D=25 nm, similar to that of FIG. 2(b), but its W is increased to 15 nm.

The present invention therefore also discloses and provides Raman sensor substrates produced by the method according to paragraphs 24-26.

Finally, this invention discloses apparatus suitable for use to measure surface-enhanced Raman spectra of molecules. Such apparatus comprises at least the following components:

(a) a radiation (or laser) source;

(b) a detector for detecting scattered radiation; and (c) a Raman sensor comprising a substrate produced in accordance with paragraphs 24-26.

One skilled in the art would know to select the appropriate wavelength of the monochromatic laser light to match the optical constants of particular metal particles used, thereby optimizing the generation of a plasmon field.

As an example, the method and apparatus of the present invention may be employed as follows: a trace chemical is deposited on the SERS-active substrate of this invention; a sensor is illuminated from below by the excitation laser to generate a plasmon field in the metal particles; the plasmon field couples with nearby analyte molecules, generating Raman photons, which are then collected and detected by a detector and displayed as a function of energy to produce a spectrum that is unique to the analyte; and the spectrum identifies the analyte, while the intensities of the band quantify the analyte.

The invention will now be described in further detail with reference to the following specific, non-limiting examples.

EXAMPLE 1

Procedures of Preparing SERS-Active Substrate

Figure 5:
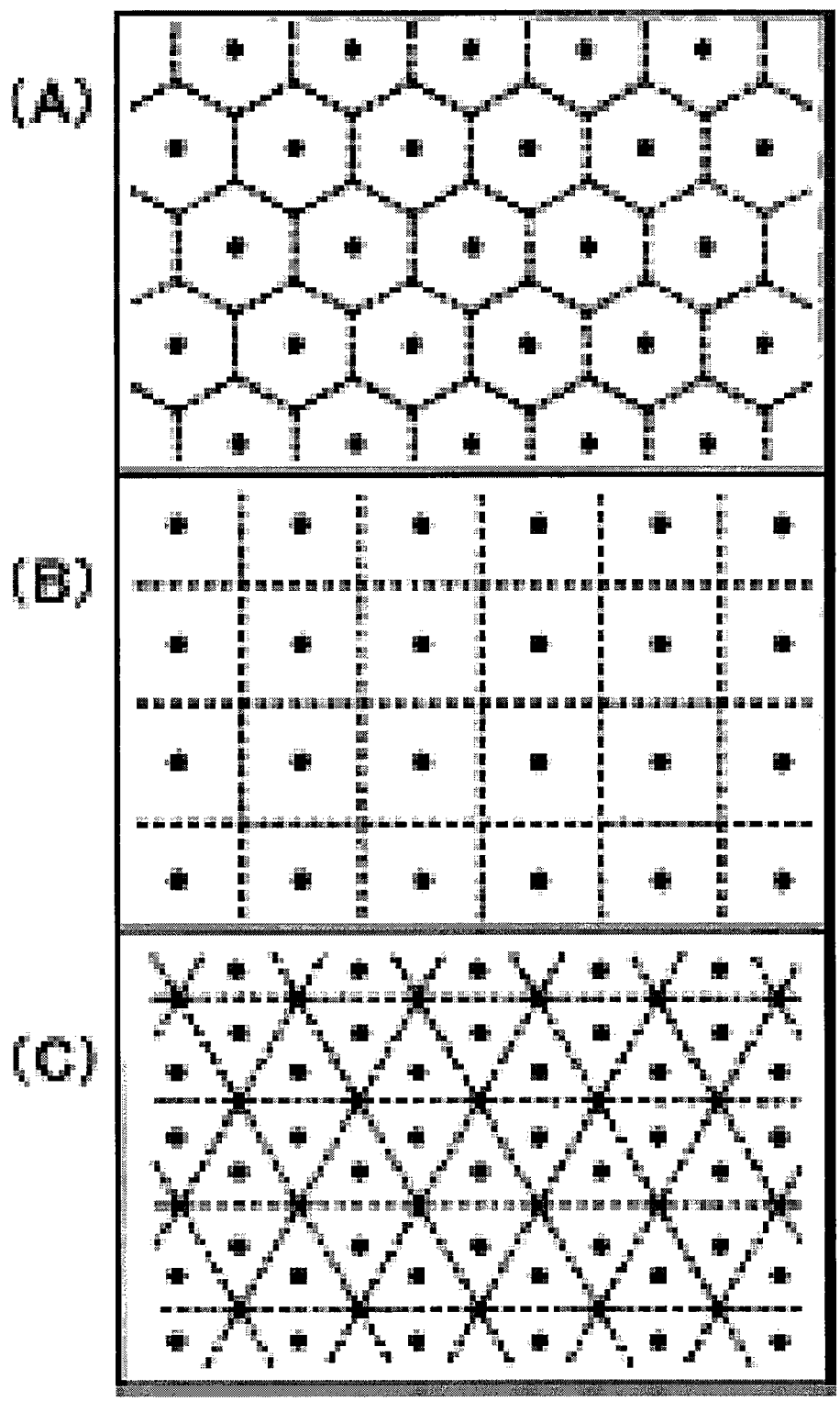
FIG. 5(a)-(c) is an illustration of the various possible arrays of pits on the AAO substrates of this invention.

High purity (99.99%) annealed aluminum foil is electropolished in a mixture of $HClO_4$ and $C_2H_5OH$ (volume ratio 1:5) until the root-mean-square surface roughness of a typical $10\,\mu m^2 \times 10\,\mu m^2$ area is 1 nm, as measured by an atomic force microscope operated in contact mode. The foil is then anodized in sulfuric acid (0.3 M) at 5° C. using a voltage in the range between 10-30 V to achieve the growth of an array of pits in the AAO substrate. See FIG. 1(b). The pits in the AAO substrate are then enlarged. For example, the substrate may be etched in 5% phosphoric acid to increase the diameters of the pits. See FIG. 1(c). By carefully controlling the etching process, arrays of pits with 5±2 nm inter-pit spacing (W) are achieved. See FIG. 1(f). An electrochemical plating procedure is then employed to grow Ag-nanoparticles into the AAO substrates. See FIG. 1(d). For growing Ag-nanoparticles into the AAO pits, an alternating current (AC) (9 V) electrochemical plating procedure is employed to the AAO substrates using electrolyte solution of silver nitrate (0.006 M) and magnesium sulfate (0.165 M) mixture with a PH value of 2, as set by the addition of sulfuric acid. After depositing Ag-nanoparticles on the AAO film, the upper layer of the AAO film is etched away again, as shown in FIG. 1(e). The final geometry of the array of Ag-nanoparticles partially embedded on an AAO substrate is shown schematically in FIG. 1(f), where S, D, and W are the distance between the centers of the adjacent nanoparticles, particle diameter, and interparticle or interpit gap, respectively. FIGS. 1 (a) to (d) shows schematically the procedure for fabricating arrays of Ag-nanoparticles separated by tunable gaps on an anodic aluminum oxide (AAO) substrate with self-organized hexagonal closed-packed array of nanopores or pits. FIG. 5(a) shows the hexagonal closed-packed structure, and FIGS. 5(b) and 5(c) show other structures.

EXAMPLE 2

Procedure for Carrying Out SERS Analysis

Raman spectroscopy measurements are performed on a micro-Raman setup with an argon ion laser at 514.5 nm. After passing through a narrow bandpass filter to remove residual plasma lines, the laser beam is focused by a 100× water-immersion objective lens (N.A.=0.95) to a ~1 μm spot in a drop of the desired solution on a Ag/AAO substrate with a corresponding beam intensity of ~$10^5$ W/cm$^2$. The scattering radiation, after being collected by the same objective lens, is sent through a Raman notch filter to a 64-cm monochromator. The dispersed spectrum is then detected by a $LN_2$-cooled charge-coupled device (CCD) camera. The low laser power density used for the measurements eliminates the side effects of local heating, deformation of Ag-nanoparticles, and photo-oxidation during laser illumination.

EXAMPLE 3

Testing the Raman Enhancing Power of the Ag/AAO Substrate

Figure 3A:
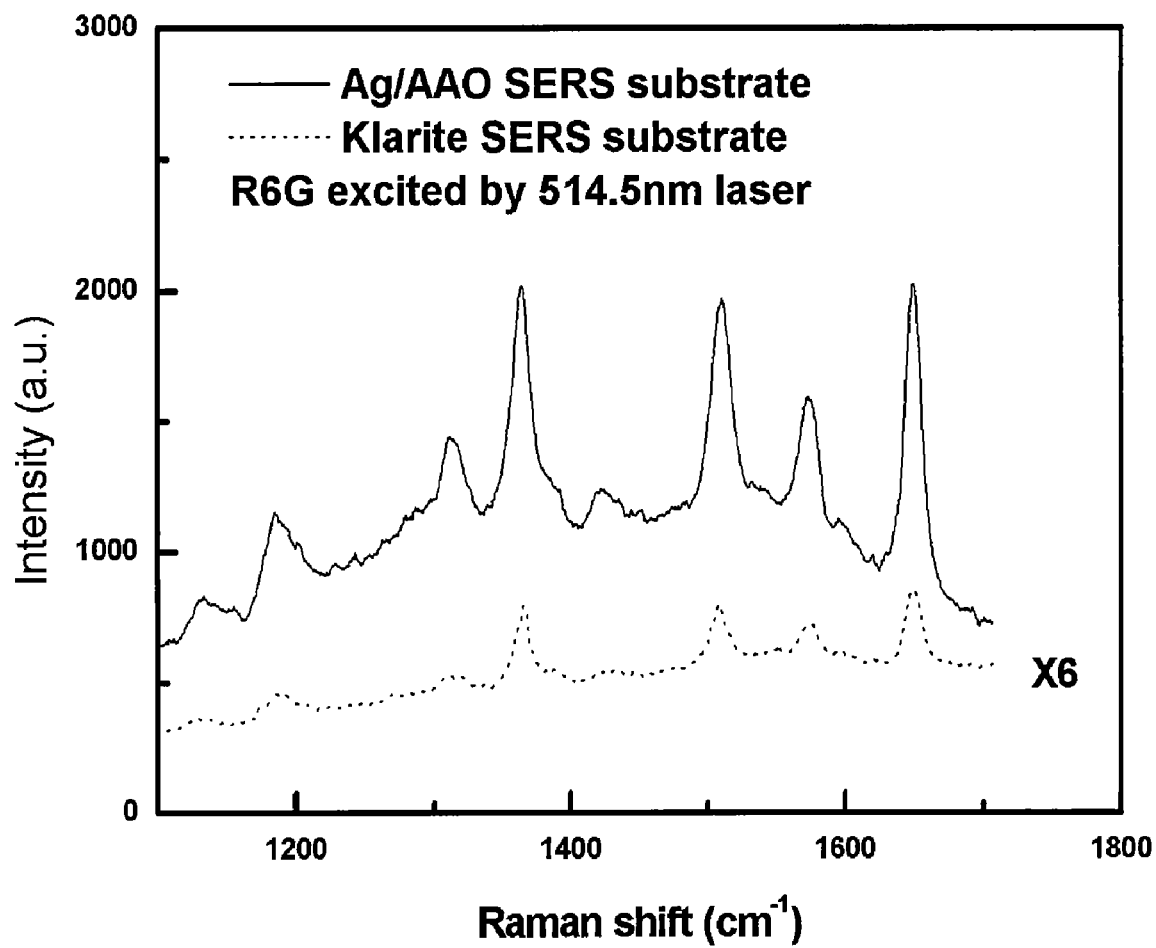
FIG. 3A depicts an SERS spectrum of $10^{-6}$ M rhodamine 6G solution on an Ag/AAO substrate.

To test the Raman enhancing power of the Ag/AAO substrates, water solution ($10^{-6}$ M) of rhodamine 6G (R6G) is applied to a substrate with $W$=5 nm and $D$=25 nm, and SERS spectrum is recorded. As shown in FIG. 3A, very large Raman peaks are observed when the fluorescence background is quenched to a steady state in a few minutes after the application of the solution. The large SERS signal indicates that the R6G molecules near the Ag-nanoparticles are excited by the laser-induced surface plasmon, while the fluorescence quenching suggests that some of R6G analyte had been spontaneously adsorbed onto the surface of nanoparticles. As shown in FIG. 3A, the enhancement factor of the Ag/AAO substrate is at least $10^5$ times larger than that of a SERS substrate prepared by depositing ~30 nm of Ag onto a silicon surface, which does not provide any detectable SERS signal above the fluorescence background. The above-mentioned enhancing power is uniformly observed over the entire sample of 1 cm$^2$ with less than 5% variation. Such enhancing power of the Ag/AAO substrates can be reached with different batches of substrates prepared by the same processing parameters, illustrating the overall consistency and reliability of the Ag/AAO substrates. In fact, the low variation of the enhanced Raman signal over various substrates further indicates that uniform molecular adsorption can be achieved with the present innovative fabrication procedure.

EXAMPLE 4

Figure 3B:
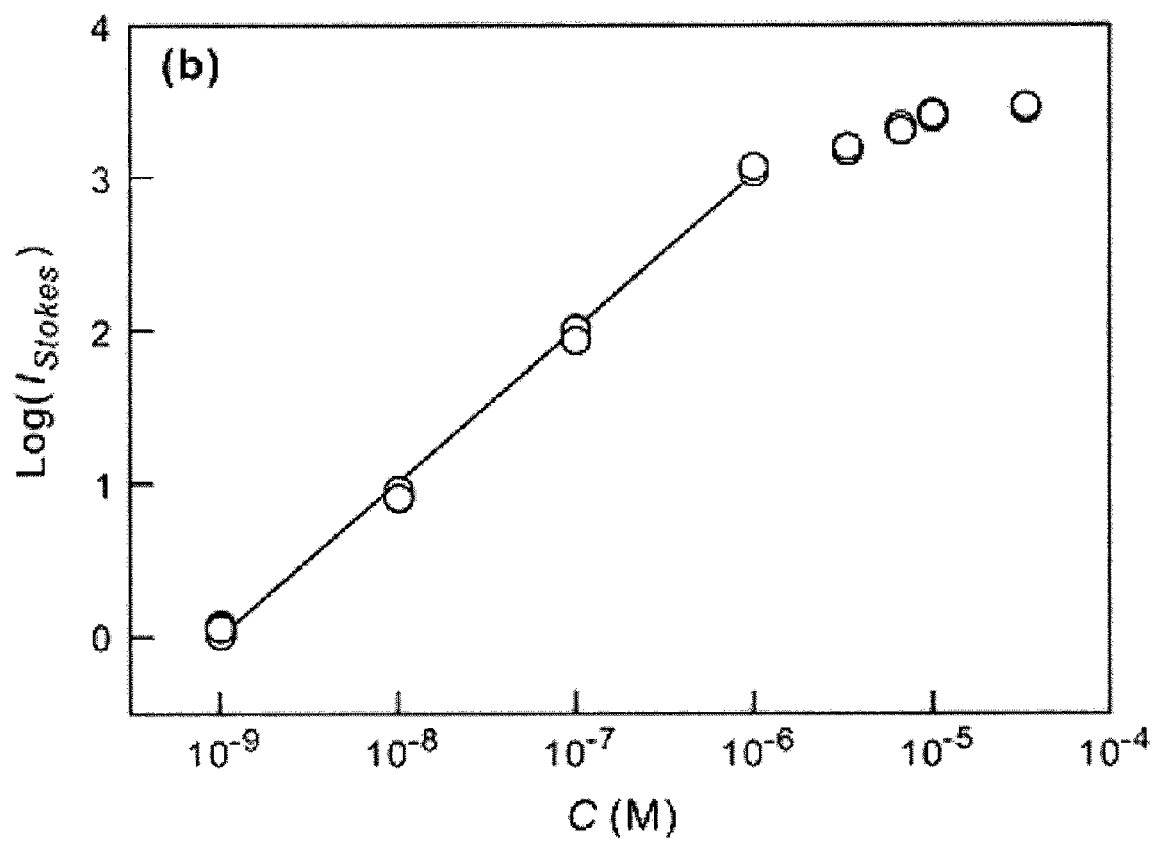
FIG. 3B illustrates the SERS signal ($I^{Stokes}$ in logarithmic scale) at 1509 cm$^{-1}$ as a function of molecular concentration in logarithmic scale.

Testing of the Enhancing Power of the Substrates with Different Concentrations of Analyte Solutions of R6G with different concentrations ($10^{-9}$ to $6.7 \times 10^{-5}$ M) are used to study the SERS dynamical range of the Ag/AAO substrates. FIG. 3B shows the Raman peak intensity (at 1509 cm$^{-1}$) vs. the R6G concentration (C). While a nonlinear dependence exists for R6G concentrations above $10^{-6}$ M, indicating that the adsorption of R6G onto the adsorption sites becomes saturated beyond this level, the linear relation between the SERS signal (log $I_{Stokes}$) and R6G concentration ranging from $10^{-9}$ to $10^{-6}$ M, suggests that the number of the adsorption sites with high Raman enhancement is large enough to accommodate a considerable range of sample concentrations.

EXAMPLE 5

Dependence of the Enhancing Power of a SERS-Active Substrate on the Value of W (the Interparticle Gap)

Figure 4A:
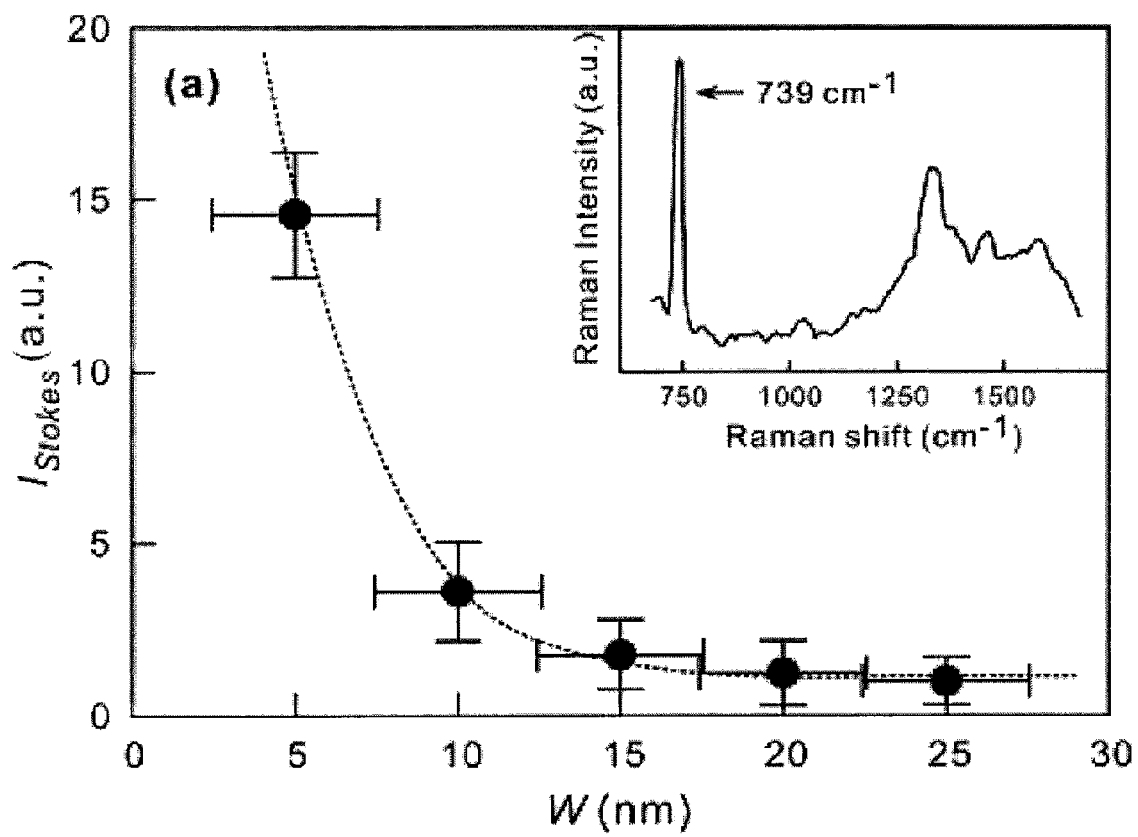
FIG. 4A depicts the integrated Raman intensity of adenine at 739 cm$^{-1}$ as a function of interparticle gap width (W) for different Ag/AAO substrates.

Water solution of adenine ($10^{-4}$ M) is used to probe dependence of Ag/AAO substrates' Raman enhancing power on the geometry of the Ag-nanoparticle array, and to study the "hot-junctions" that are believed to exist between two nanoparticles with a gap below 10 nm. Adenine is chosen because it does not have any appreciable one-photon absorption at the excitation wavelength and therefore has very low fluorescence background that interferes with SERS measurement. Typical SERS spectrum of adenine on Ag/AAO substrates, as shown by the inset of FIG. 4A, has two prominent Raman peaks at 739 and 1330 cm$^{-1}$, corresponding to the purine ring breathing mode and the CN stretching mode, respectively.[21,22]

As W is reduced below 25 nm with D fixed at 25 nm, the Raman peaks increase slowly in the beginning, significantly at W=10 nm, and dramatically when W reaches an unprecedented small value of 5 nm, as demonstrated by the integrated 739 cm$^{-1}$ peak in FIG. 4A.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preparing a substrate with metal particles, effective for surface enhanced Raman spectroscopy (SERS) comprising the steps of:
    (a) preparing a template comprising an array of pits;
    (b) etching the template to enlarge the pits in the template, such that the adjacent, enlarged pits are separated by 3-50 nanometers;
    (c) depositing metal particles into the pits on the template; and
    (d) further etching the template to manifest the metal particles.

2. A method according to claim 1, wherein said enlarged pits are no more than about 100 nanometers in diameter.

3. A method according to claim 2, wherein said metals are Group IB metals.

4. A method according to claim 3, wherein said step (a) comprises anodizing said template.

5. A method according to claim 3, wherein said step (c) comprises electrochemically plating the metal particles onto the said template.

6. A method according to claim 3, wherein said template is an anodic aluminum oxide (AAO) template.

7. A substrate produced by the method of claim 3.

8. The substrate according to claim 7, wherein the metal particles are arranged in a symmetric geometry.

9. The substrate according to claim 8, wherein the symmetric geometry is a hexagonal or tetragonal closed-packed structure.

10. A Raman instrument comprising:
    (a) a radiation source;
    (b) a detector for detecting scattered radiation; and
    (c) a Raman sensor comprising a substrate of claim 3.

11. The Raman instrument according to claim 10, wherein the substrate comprises metal particles arranged in a symmetric geometry.

12. The Raman instrument according to claim 11, wherein the symmetric geometry is a hexagonal or tetragonal closed-packed structure.

* * * * *